(12) United States Patent
Henckel et al.

(10) Patent No.: US 6,585,634 B1
(45) Date of Patent: Jul. 1, 2003

(54) FORCE SENSING MECHANISM

(75) Inventors: John Eric Henckel, Houston, TX (US); Richard T. Thornton, League City, TX (US); JoLynn R. Thornton, League City, TX (US); Anthony J. Bradshaw, Duluth, GA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 50 days.

(21) Appl. No.: 09/836,404

(22) Filed: Apr. 17, 2001

(51) Int. Cl.⁷ .................................................. A61N 5/00
(52) U.S. Cl. ............... 600/7; 600/1; 600/3; 73/862.627
(58) Field of Search ................................ 600/1, 3, 7, 2, 600/4; 338/2, 5; 73/862.045, 862.627

(56) References Cited

U.S. PATENT DOCUMENTS

| | | | |
|---|---|---|---|
| 3,724,274 A | * | 4/1973 | Millar ........................ 338/4 X |
| 4,858,615 A | | 8/1989 | Meinema |
| 4,881,937 A | | 11/1989 | Van Hooft et al. |
| 5,059,166 A | | 10/1991 | Fischell et al. |
| 5,176,617 A | | 1/1993 | Fischell et al. |
| 5,605,530 A | | 2/1997 | Fishell |
| 5,851,172 A | | 12/1998 | Bueche et al. |
| 6,048,300 A | | 4/2000 | Thornton et al. |
| 6,061,588 A | * | 5/2000 | Thornton et al. ........... 600/424 |

OTHER PUBLICATIONS

U.S. patent application Ser. No. 09/749,710, Neale et al., filed Dec. 27, 2000.
U.S. patent application Ser. No. 09/836,646, Henckel et al., filed Apr. 17, 2001.

* cited by examiner

*Primary Examiner*—Kevin Lee
(74) *Attorney, Agent, or Firm*—Blakely, Sokoloff, Taylor & Zafman LLP

(57) ABSTRACT

A force sensing mechanism. The mechanism is provided with a beam having a stationary portion. A housing accommodates a portion of a device coupled to an afterloader and is coupled to the beam. A force sensor coupled to the beam monitors a force of the device. An afterloader system includes a processor and a cartridge to house the force sensing mechanism. In a method, the force sensing mechanism is provided to which a portion of a device coupled to an afterloader is coupled. A device force of the device is monitored.

23 Claims, 3 Drawing Sheets

FORCE SENSING MECHANISM

BACKGROUND OF THE INVENTION

The present invention relates to afterloaders and devices to couple to afterloaders. In particular, the present invention relates to the sensing of force related to a device coupled to an afterloader.

BACKGROUND OF THE RELATED ART

In the last several years, minimally invasive surgical procedures have become increasingly common. Treatment of vasculature can be done in a minimally invasive manner. For example, a blood vessel narrowed by an obstruction, such as a stenotic lesion, can be treated by an angioplasty procedure to compress the lesion and widen the vessel to increase blood flow there through. Angioplasty involves the advancement of an angioplasty balloon at the distal end of a catheter to the site of the lesion within the vessel. Once positioned, the balloon is inflated to compress the lesion.

Following angioplasty, the risk of a subsequent restenosis is significant. Restenosis, the re-emergence of a stenotic lesion, is prone to occur at the site of the former stenotic lesion treated by the angioplasty. In order to help avoid restenosis, radiotherapy procedures have been developed that are applied to the site of the former stenosis following angioplasty. These procedures include the advancement of a radiation source to the site of the former stenosis. Application of radiation to the site of the former stenosis can significantly reduce the risk of restenosis.

Radiotherapy can include the use of a radiation source wire as well as other radiation sources. Where a source wire is used, it will be made available to the physician in a secure manner and delivered to a patient by way of a radiotherapy catheter that can be equipped with a centering balloon. The centering balloon will be positioned within vasculature at the site of the former stenosis. The source wire will be advanced through a lumen of the radiotherapy catheter to a distal portion of the catheter. The centering balloon helps keep the catheter lumen centered to allow a more even distribution of radiotherapy.

The source wire is advanced by way of an afterloader. That is, the source wire has been loaded within an afterloader prior to treatment. The afterloader is a machine which stores the source wire and subsequently advances it through a radiotherapy catheter to deliver radiotherapy. The afterloader advances and retracts the source wire through the radiotherapy catheter in an automated manner during the radiotherapy procedure.

It is important that the radiotherapy catheter be positioned such that its lumen is un-kinked and unobstructed as the source wire is advanced there through. For example, if a given automated radiotherapy procedure is carried out with an obstructed lumen, the source wire could be damaged, or worse, pierce the radiotherapy catheter as it attempts to force itself past the obstruction. This could result in directly exposing vasculature to the source wire in an unintended manner and possible harm to the patient. Additionally, placement of the radiotherapy catheter within a highly tortuous vessel can lead to similar consequences if the advancing source wire exerts a force on the catheter that either the catheter or the source wire cannot tolerate.

In addition to a radiotherapy catheter, other devices can be connected to the afterloader to receive an advancing source wire. For example, a physics coupler can be secured to the afterloader to establish measurements or perform calibrations related to the source wire prior to application of a radiotherapy procedure. Additionally, oncology applicators can be secured to the afterloader to receive the source wire. Regardless of the device coupled to the afterloader, an unobstructed lumen will be required.

In order to ensure that the lumen of the device coupled to the afterloader is positioned in a smooth and unobstructed manner when receiving the advancing source wire, the afterloader can be equipped with a dummy wire. The dummy wire, having no radioactive source, can be advanced through the lumen and retracted again to ensure a clear lumen path is present to receive the source wire.

However, the dummy wire, like the source wire, is also susceptible to damage and can cause injury to a patient should it exert a force upon the device coupled to the afterloader that the device or the dummy wire cannot tolerate. Therefore, what is needed is a force sensing mechanism to monitor force in relation to the device.

SUMMARY OF THE INVENTION

An embodiment of the present invention provides a force sensing mechanism having a beam with a stationary portion. A housing for an afterloader with a coupling portion to accommodate a portion of a device coupled to the afterloader is coupled to the beam and a force sensor is also coupled to the beam to monitor a force of the device.

An embodiment of the invention includes an afterloader system with a processor and a force sensing mechanism to deliver information to the processor regarding a force of a device coupled to an afterloader. The system includes a cartridge to house the force sensing mechanism.

In a method of the invention a force sensing mechanism having a beam with a stationary portion is provided. A portion of a device is coupled to a housing for an afterloader and the housing coupled to the beam. A device force of the device is monitored.

DETAILED DESCRIPTION OF THE INVENTION

While the background of the present invention is described with reference to certain afterloaders and radiotherapy catheters, the invention is applicable to any situation where a device to receive an advancing source is coupled to a device advancing the source. This would include various forms of brachytherapy devices and other larger radiotherapy systems. The invention is particularly useful when the device to receive the advancing source is susceptible to kinking or to puncture as a result of the advancing.

Figure 1:
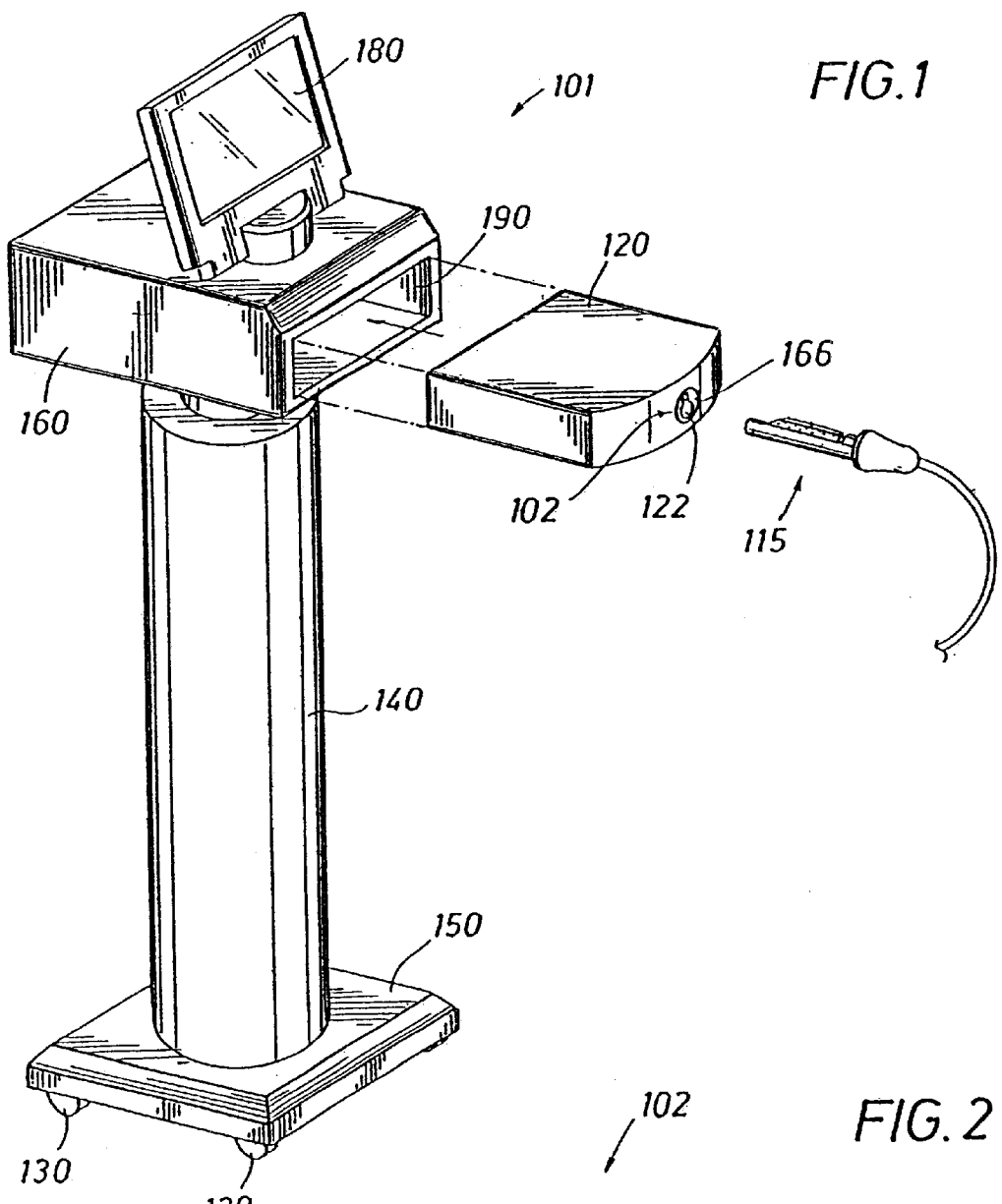
FIG. 1 is a perspective view of an afterloader having an embodiment of a force sensing mechanism of the present invention.

Referring to FIG. 1, a perspective view of an embodiment of an afterloader 101 is shown. The afterloader 101 includes a head platform 160 with a monitor 180. The monitor 180 shown is a touch screen that allows a physician to interact with a computer program to direct a radiotherapy procedure. The head platform 160 of the embodiment shown includes a processor to execute application programs and respond to user input at the touch screen monitor 180. The processor also operates in conjunction with a force sensing mechanism 102 discussed further herein. In other embodiments of the invention signals are received from other sources as well. The head platform 160 is atop a pedestal 140 that is mounted to a base 150 having wheels 130.

A cartridge 120 of the afterloader 101 is included to be plugged into a cartridge holder 190. The cartridge 120 contains a source wire 305 to be used during a radiotherapy or other procedure (see FIG. 3). In other embodiments of the invention a radioactive source is delivered by implements other than a source wire, such as in the form of ribbons or pellets.

The cartridge 120 of the afterloader 101 is to accommodate a portion of a device to couple to the afterloader 101. In the embodiment shown, the device is a radiotherapy catheter 115. However, in other embodiments of the invention, other devices are used. For example, in one embodiment the device is to aid in establishing calculations related to the source wire 305 (see FIG. 3) prior to a radiotherapy procedure. This device is often referred to as a physics coupler. In another embodiment of the invention, the device is an applicator for use in oncology treatment.

Figure 2:
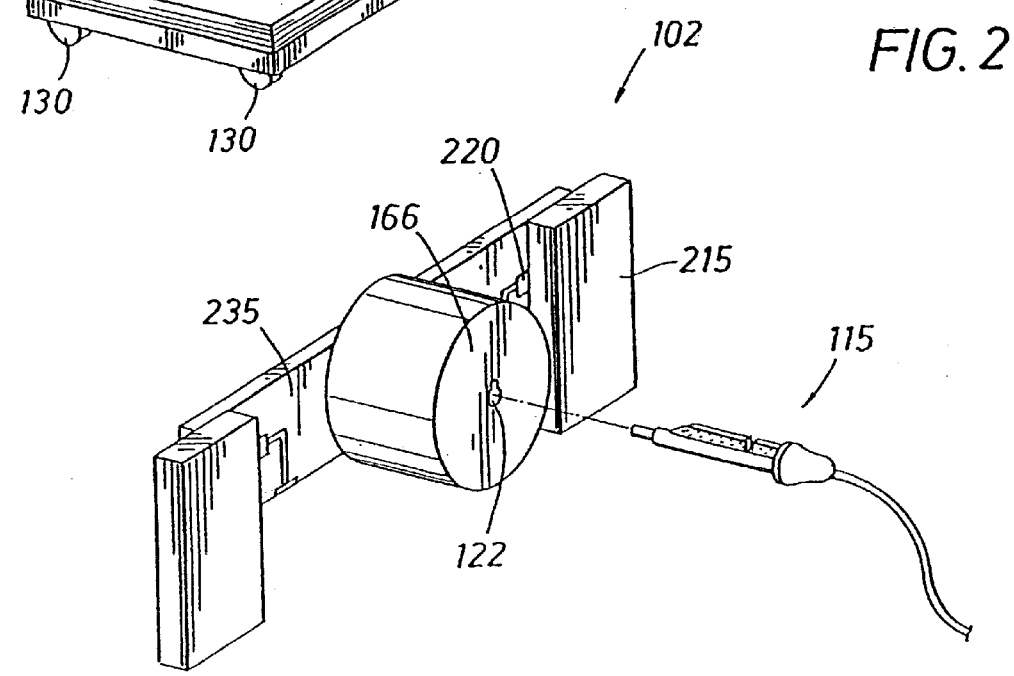
FIG. 2 is a perspective view of the force sensing mechanism of FIG. 1 to receive a device to couple to the afterloader.

Continuing with reference to FIG. 1, and further detailed in FIG. 2, the afterloader 101 is equipped with an embodiment of a force sensing mechanism 102. The force sensing mechanism 102 includes a housing 166 having a coupling portion to receive a portion of the radiotherapy catheter 115. In the embodiment shown, the coupling portion is a receptacle 122. The force sensing mechanism 102 detects forces of the radiotherapy catheter 115 exerted toward or away from the receptacle 122 as discussed further herein.

Referring to FIG. 2, a perspective view of the force sensing mechanism 102 of FIG. 1 is shown. The housing 166 is mounted to a lateral beam 235. Each end of the beam 235 is held by stationary supports 215.

Figure 5:
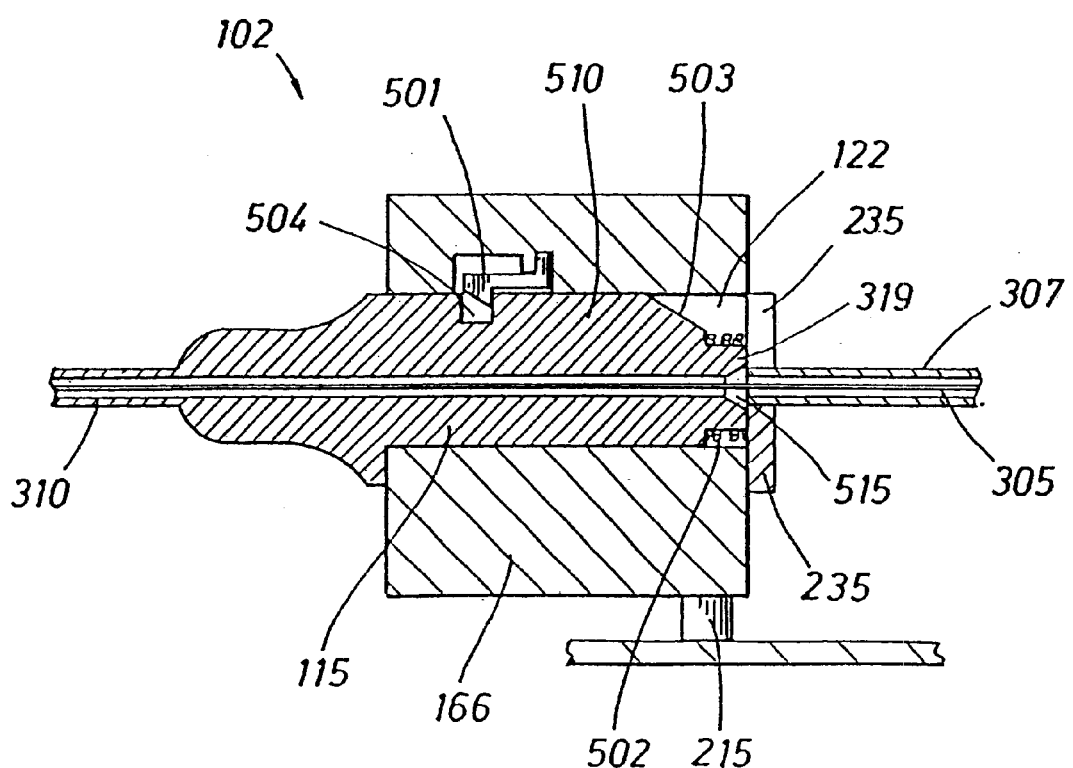
FIG. 5 is a cross-sectional side view of the force sensing mechanism of FIG. 3.

The receptacle 122 accommodates and secures the received portion of the radiotherapy catheter 115 in place during a radiotherapy procedure (see FIG. 5). As discussed further herein, the beam 235 is responsive to forces of the plugged in radiotherapy catheter 115, such as a pulling force exerted on the beam 235 by the housing 166 where the radiotherapy catheter 115 is forced in a direction away from the receptacle 122. This responsiveness of the beam 235 is sensed by one or more force sensors 220 coupled to the beam 235.

Figure 3:
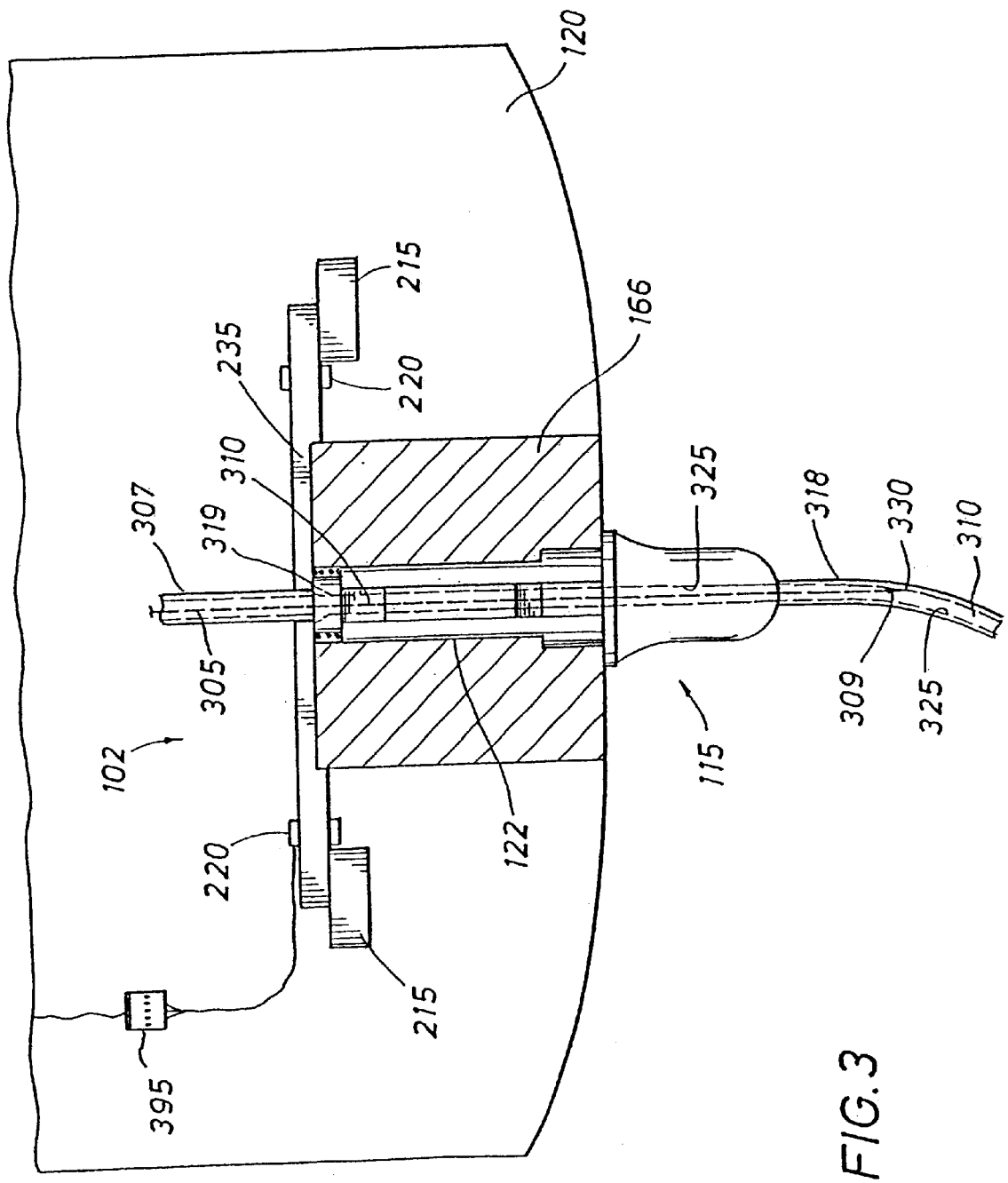
FIG. 3 is a cross-sectional view of the cartridge of FIG. 2 revealing an embodiment of a force sensing mechanism.

Referring to FIG. 3, a cross-sectional view of the cartridge 120 is shown. The cartridge 120 includes the force sensing mechanism 102 to detect forces exerted by the radiotherapy catheter 115.

In the embodiment shown, a portion of the radiotherapy catheter 115 is secured within a receptacle 122 of a housing 166 of the cartridge 120. The receptacle 122 aligns a proximal extension 319 of the radiotherapy catheter 115 with a tubular output guide 307 from which a source wire 305 having a radiation source 309 is advanced. The radiotherapy catheter 115 is equipped with a catheter lumen 310 to receive the source wire 305. The catheter lumen 310 runs from the proximal extension 319 and through a body 318. In one embodiment, the radiotherapy catheter 115 has a balloon portion at a distal end of the body 318 that is positioned across the site of a former stenosis in a vessel of a patient for delivery of radiotherapy thereat.

Referring to FIGS. 1–3, during an automated radiotherapy procedure of the invention, in which radiotherapy is to be delivered to the site of a former stenosis, the source wire 305 is advanced through the tubular output guide 307 and through the catheter lumen 310 of the radiotherapy catheter 115. The radiotherapy procedure is automated and directed, in part, by the physician through a user interface, such as the touch screen monitor 180.

As the source wire 305 is advanced and guided through the catheter lumen 310 during a radiotherapy procedure, it can come into contact with a lumen wall 325 of the catheter lumen 310. For example, where the body 318 of the radiotherapy catheter 115 bends, the advancing source wire 305 will contact the lumen wall 325 (e.g. at impact point 330) and subsequently bend to conform to the contour and direction of the catheter lumen 310.

When the advancing source wire 305 contacts the lumen wall 325, an active force is exerted against the lumen wall 325 of the radiotherapy catheter 115 by the advancing source wire 305. Likewise, the lumen wall 325 may provide frictional resistance to the advancing source wire 305. Within certain limits the active force of the advancing source wire 305 will be sufficient to allow the source wire 305 to continue advancing. That is, in spite of opposing forces being exerted, such as the active force described here and the frictional resistance discussed above.

Due to the opposing forces described above, the radiotherapy catheter 115 will tend to move in the direction of the advancing source wire 305. However, as also noted above, the radiotherapy catheter 115 is secured at the receptacle 122 of the housing 166. Therefore, the tendency of the radiotherapy catheter 115 to move in the direction of the advancing source wire translates to a pull on the housing 166 in this same direction. Because the housing 166 is secured to the beam 235, the pull on the housing 166 is felt by the beam 235 as a pull on the beam 235. Thus, this pulling force is sensed by the force sensors 220 coupled to the beam 235.

The force exhibited by the radiotherapy catheter 115 as it tends to move toward or away from the receptacle 122 is referred to here as a responsive force. This is to distinguish this force from forces such as the active forces displayed by an advancing source wire 305, described above, which can act upon the radiotherapy catheter 115. That is, the responsive force displayed by the radiotherapy catheter 115 is in response to the active force exerted by the advancing source wire 305 upon the radiotherapy catheter 115 (e.g. at lumen wall 325 of FIG. 3). It is this responsive force exerted by the radiotherapy catheter 115 which is sensed at the force sensors 220 and accounted for by the force sensing mechanism 102.

The responsive force displayed by the radiotherapy catheter 115 can be in response to forces acting upon the radiotherapy catheter 115 other than an advancing source wire 305. For example, in one embodiment of the invention, the responsive force displayed by the radiotherapy catheter 115 is the result of external manipulation or tugging on the radiotherapy catheter 115 as discussed further herein. Additionally, the responsive force displayed by the radiotherapy catheter 115 may be in a direction toward the receptacle 122, again as a result of external manipulation or pushing on the radiotherapy catheter 115 as also discussed further herein. That is, even a responsive force in a direction toward the receptacle 122 will be translated to the beam 235 and sensed by the force sensors 220.

The degree or amount responsive force exhibited by the radiotherapy catheter 115 can be affected by several factors. For example, the strength and speed of an advancing source wire 305 along with the durability and surface characteristics of the lumen wall 325 can affect the responsive force exhibited by the radiotherapy catheter 115 in response to the advancing source wire 305. Additionally, a highly tortuous path or a kink in the catheter lumen 310 can greatly increase the responsive force displayed by the radiotherapy catheter 115 as the source wire is advanced. Therefore, placement of the radiotherapy catheter 115 within a highly tortuous vessel can affect the force displayed by the radiotherapy catheter 115 as a source wire 305 is advanced.

As described further herein, embodiments of the force detection mechanism 102 detect the responsive force exerted by the radiotherapy catheter 115 to prevent piercing of the radiotherapy catheter 115 by an advancing source wire 305. The force detection mechanism 102 also helps to prevent damage to the advancing source wire 305. Detection of this responsive force displayed by the radiotherapy catheter 115 can provide a more accurate and direct account of the condition of the radiotherapy catheter 115 than, for example, detection of the active force required to advance the source wire 305. This is because the active force required for advancement of the source wire 305 may be affected by factors outside of the radiotherapy catheter 115 (e.g. within the afterloader 101 (see FIG. 1)). Detection of the responsive force provides a more direct measurement of forces actually related to the radiotherapy catheter 115.

As noted above, the responsive force displayed by the radiotherapy catheter 115 can result from factors other than an advancing source wire 305. External manipulation of the radiotherapy catheter 115, such as actual pulling (distally) or pushing (proximally) on the radiotherapy catheter 115 (e.g. by a physician or patient during a radiotherapy procedure) can cause the responsive force of the radiotherapy catheter 115 to be sensed.

Continuing with reference to FIGS. 1–3, the configuration of one force sensing mechanism 102 embodiment is discussed in further detail. The beam 235 is mounted to stationary supports 215. The stationary supports 215 are secured to the cartridge 120 and immobile providing a robust and stable configuration to the force sensing mechanism 102. The housing 166 is similarly mounted to the beam 235. However, the beam 235 is not entirely immobile. For example, when a responsive force pulls the housing 166 in a distal direction (e.g. away from the receptacle 122) the beam 235 will bend in a distal direction. Likewise, when a force pushes the housing 166 in a proximal direction the beam 235 will bend in a proximal direction. In one embodiment of the invention, the housing 166 and the beam 235 are of unitary construction having stationary portions and further capable of bending and directly securing a portion of the radiotherapy catheter 115.

As described above, advancement of the source wire 305 can lead to a responsive force displayed by the radiotherapy catheter 115 in the direction of this advancement. However, in the embodiment shown, the radiotherapy catheter 115 is secured within the receptacle 122 of the housing 166 and unable to move significantly in any direction. Therefore, this responsive force of the radiotherapy catheter 115 is translated to the housing 166. In other words, this responsive force can lead to the force pulling the housing 166 in a distal direction as described above. Therefore, the beam 235 is susceptible to bending in a distal direction during advancement of the source wire 305.

The bending, or strain, upon the beam 235 resulting from force exerted upon the housing 166 is monitored by force sensors 220. The strain is directly related to the materials and thickness of the beam 235. In the embodiment shown, the force sensors 220 are strain gauges. The force sensors 220 are electronically coupled to a Printed Circuit Board (PCB) 395 which translates beam 235 strain information to the processor of the afterloader 101. As discussed further herein, this information can be accounted for and factored into an ongoing procedure of the afterloader 101.

As mentioned above, beam 235 strain information is fed to the processor of the afterloader 101. This information can be used during a procedure to slow down the advancing source wire 305 or stop its advancement altogether where necessary to prevent damage to the source wire 305 or the radiotherapy catheter 115.

In one embodiment of the invention, the advancing source wire 305 is slowed down where between about 1.1 and 1.2 pounds of force is detected by the force sensing mechanism 102. That is, a slow-down force of between about 1.1 and 1.2 pounds is programmed into the processor of the afterloader 101 and accounted for during advancement of the source wire 305 during a procedure.

In one embodiment of the invention, the advancing source wire 305 is stopped from advancing where between about 1.3 and 1.5 pounds of force is detected by the force sensing mechanism 102. That is, a stop force of between about 1.3 and 1.5 pounds is programmed into the processor of the afterloader 101 and accounted for during advancement of the source wire 305 during a procedure. In another embodiment of the invention, the stop force does not actually cause the source wire 305 to stop advancing until successive readings of the stop force have taken place. For example, in one embodiment, the source wire 305 is caused to stop advancing upon about 5 successive detections of the predetermined stop force.

In one embodiment of the invention, the slow-down force and the stop force change during the same procedure depending upon where the distal portion of the source wire 305 is within the radiotherapy catheter 115. For example, in one embodiment of the invention the stop force is between about 1.3 and 1.5 pounds where the distal portion of the source wire 305 is advanced less than about 1800 millimeters into the radiotherapy catheter 115 and between about 2.4 and 2.6 pounds where the distal portion of the source wire 305 is advanced more than about 1800 millimeters into the radiotherapy catheter 115. This changing stop force accounts for the fact that the source wire 305 is naturally expected to encounter more resistance, increasing the responsive force of the radiotherapy catheter 115, as the source wire 305 advances through highly tortuous vasculature once within the body of a patient.

Figure 4:
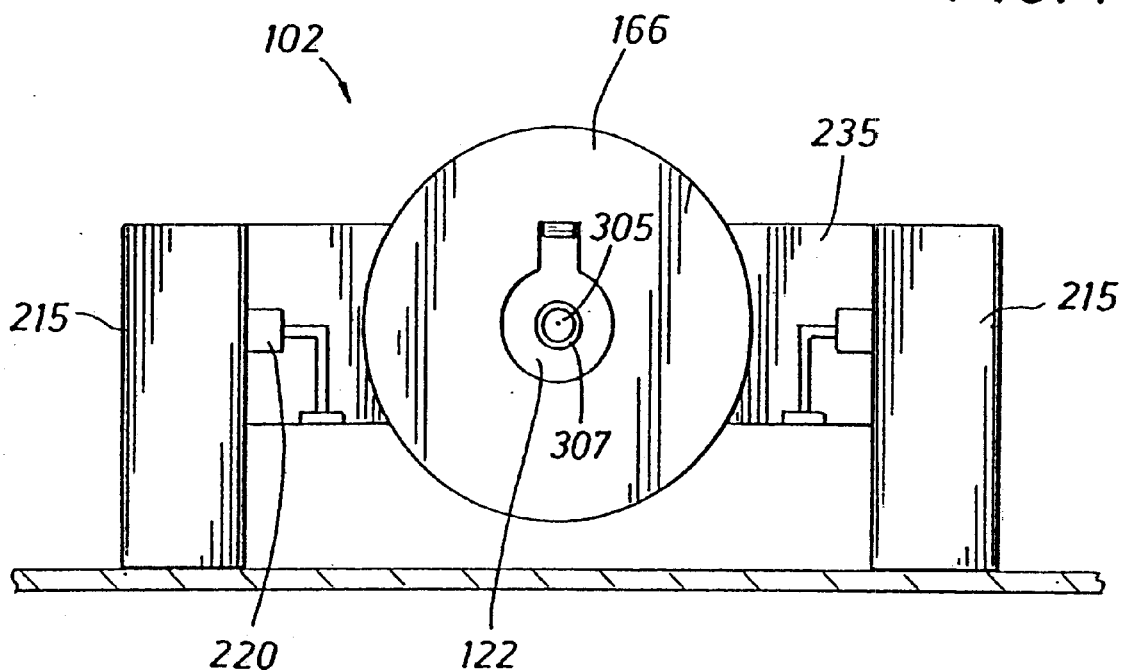
FIG. 4 is a front plan view of the force sensing mechanism of FIG. 3.

Referring to FIG. 4, a front view of the force sensing mechanism 102 of FIGS. 2 and 3 is shown. The housing 166 is suspended by the beam 235 and other support of the housing 166 is avoided. In this manner, forces exerted on the housing 166 can be translated directly to the beam 235 without interference. The housing 166 includes the receptacle 122. The beam 235 includes the sensors 220 and is mounted to the stationary supports 215. From this view the tubular output guide 307 and source wire 305 can also be seen.

In the embodiment shown, the force sensors 220 are distributed on the beam 235 uniformly equidistant from a location adjacent the receptacle 122. The housing 166 is disposed centrally on the beam 235 between the stationary supports 215. The receptacle 122 is located centrally within the housing 166. For each force sensor 220 to one side of the receptacle 122 there is a corresponding force sensor 220 to the opposite side of the receptacle 122 equidistant from a location adjacent the receptacle 122. This configuration helps ensure accurate force sensing detection. That is, the net force detected by the force sensing mechanism 102 will be in line with the radiotherapy catheter 115 (see FIG. 3) and thus, in line with the responsive force displayed thereby. In the embodiment shown, 4 force sensors 220 are distributed about the beam 235 (2 shown). In alternate embodiments alternate numbers of force sensors 220 are utilized.

Referring to FIG. 5 a side cross sectional view of the force sensing mechanism 102 of FIG. 3 is shown. The housing 166 is shown accommodating a portion of the radiotherapy catheter 115 within the receptacle 122. The source wire 305 is shown advanced through the tubular output guide 307 and through the catheter lumen 310. A funnel opening 515 is provided at the access to the catheter lumen 310 to ensure receipt of the source wire 305 by the catheter lumen 310. The housing 166 is shown mounted to the beam 235. A stationary support 315, which mounts the beam 235, is also shown.

To ensure that the responsive force of the radiotherapy catheter 115 is translated to the housing 166 for proper responsive force detection, a portion of the radiotherapy catheter 115 is tightly secured within the receptacle 122. The housing 166 includes a latch 501 that is deflected upward by an incline 503 of the radiotherapy catheter 115 during insertion into the receptacle 122. The radiotherapy catheter 115 includes a notch 504 that, when traversing the latch 501, allows the latch 501 to slide back downward and into the notch 504 to secure the radiotherapy catheter 115 in place. A spring 502 of the housing 166 is included to be positioned around the proximal extension 319 of the radiotherapy catheter 115 and bias the proximal-most portion of the radiotherapy catheter 115 securely toward the latch 501. Thus, the portion of the radiotherapy catheter 115 received by the housing 166 is substantially immobilized. To release the radiotherapy catheter 115 from the receptacle 122 an embodiment of the invention includes an ejection mechanism to lift the latch 501.

Placement of the radiotherapy catheter 115 in the manner described above ensures precise positioning within the housing 166. Therefore, placement of the radiotherapy catheter 115 can be precisely predetermined. As such, calculations accounting for the position of the radiotherapy catheter 115 or an advancing source wire 305 relative thereto can be accurately obtained.

In one embodiment of the invention the afterloader 101 (see FIG. 1) includes an identification mechanism where the radiotherapy catheter 115 has a detectable region 510 to identify the type of radiotherapy catheter 115, based on materials and other characteristics, which has been secured to the housing 166. Embodiments of the invention include a detectable region 510 that is an optically detectable element, a transponder, a mechanically detectable irregular surface, a bar code, a memory device such as an EEPROM (Electronically Erasable Programmable Read-Only Memory) assembly or a flash memory, and a magnetic strip. Correspondingly, embodiments of the housing 166 include a region that is an optical detector, an antenna, mechanical limit switches, a bar code scanner, a memory reader such as for an EEPROM or flash memory, and a scanner to read a magnetic strip, respectively, to read the detectable region 510.

The identity information referred to above can be relayed to the processor of the afterloader 101. This information can be used to establish the slow-down force, the stop force, and other parameters of a procedure that can be affected by the type of radiotherapy catheter 115 provided. For example, the slow-down force and the stop force may be varied depending on the durability of the particular type of radiotherapy catheter 115 provided. As such, in one embodiment of the invention, the identity of the radiotherapy catheter 115 is used to establish the slow-down force of the advancing source wire 305. In another embodiment of the invention, the identity of the radiotherapy catheter 115 is used to establish the stop force of the advancing source wire 305.

Embodiments of the invention include devices and mechanisms to ensure that the lumen of a device to couple to an afterloader remains smooth and unobstructed in order for a procedure to be run with the device. Additionally, embodiments of the invention help avoid damage to an advancing source wire or other device, damage to a device coupled to an afterloader, and injury to a patient during an afterloader procedure. Although exemplary embodiments of the invention describe particular devices to couple to afterloaders, particular afterloaders, and particular procedures, additional embodiments of the invention are possible. Many changes, modifications, and substitutions may be made without departing from the spirit and scope of this invention.

We claim:

1. A force sensing mechanism comprising:

a beam having a stationary portion;

a housing for an afterloader, said housing coupled to said beam and having a coupling portion to accommodate a portion of a device to couple to said afterloader; and a force sensor coupled to said beam to monitor a force of said device, wherein said sensor is of a plurality of sensors, said stationary portion is a first stationary portion adjacent a second stationary portion of said beam, said receptacle of said housing located adjacent said beam and positioned between said first stationary portion and said second stationary portion, said plurality of sensors positioned uniformly equidistant from a location adjacent said coupling portion.

2. The force sensing mechanism of claim 1 wherein said device is selected from a group consisting of a radiotherapy catheter, a physics coupler, and an oncology applicator.

3. The force sensing mechanism of claim 1 wherein said device is to receive an advancing source implement through a lumen defined by a lumen wall of said device, said force determined in part by a factor selected from a group consisting of advancing source implement speed, advancing source implement strength, lumen wall durability, lumen wall surface character, lumen tortuousness, and device external manipulation.

4. The force sensing mechanism of claim 1 wherein said beam suspends said housing, such that said force of said device exerted on said housing is directly translated to said beam without interference.

5. The force sensing mechanism of claim 1 wherein said device includes a detectable region selected from a group consisting of an optically detectable element, a transponder, a mechanically detectable irregular surface, a bar code, a memory device, and a magnetic strip.

6. The force sensing mechanism of claim 1 wherein said housing includes a region selected from a group consisting of an optical detector, an antenna, mechanical limit switches, a bar code scanner, a memory reader, and a scanner to read a magnetic strip.

7. A force sensing mechanism comprising:

a beam having a stationary portion;

a housing for an afterloader, said housing coupled to said beam and having a coupling portion to accommodate a portion of a device to couple to said afterloader; and a force sensor coupled to said beam to monitor a force of said device, wherein said housing includes a movable latch extending into said receptacle to cooperate with a notch of said device to secure said device to said housing.

8. The force sensing mechanism of claim 7 further comprising a spring of said housing within said receptacle to bias a proximal-most portion of said device toward said latch to substantially immobilize said device between said spring and said latch.

9. An afterloader system comprising:

a processor;

a force sensing mechanism to deliver information to said processor regarding a force of a device to couple to an afterloader; and a cartridge to house said force sensing mechanism, said force sensing mechanism having a beam with a stationary portion, a housing coupled to said beam to accommodate a portion of said device, and a force sensor coupled to said beam to monitor said force of said device.

10. The afterloader system of claim 9 further comprising an identification mechanism to deliver information to said processor regarding an identity of said device.

11. The afterloader system of claim 9 wherein said device is selected from a group consisting of a radiotherapy catheter, a physics coupler, and an oncology applicator.

12. The afterloader system of claim 9 further comprising a source wire to be advanced from s aid cartridge into said device, said device including a balloon to stabilize a portion of said device within vasculature of a patient.

13. The afterloader system of claim 9 further comprising an input device coupled to said processor to select a procedure to be run.

14. The afterloader system of claim 13 wherein said input device is a touch screen monitor.

15. A method comprising:

providing a force sensing mechanism having a beam with a stationary portion and a force sensor coupled to said beam;

coupling a portion of a device to a housing for an afterloader, said housing coupled to said beam; and monitoring a device force of said device, wherein said coupling is of said portion of said first device to a predetermined precise location of said housing, said method further comprising:

withdrawing said source implement from said lumen; and connecting a portion of a second device to said precise location.

16. A method comprising:

providing a force sensing mechanism having a beam with a stationary portion and a force sensor coupled to said beam;

coupling a portion of a device to a housing for an afterloader, said housing coupled to said beam;

monitoring a device force of said device; and advancing a source implement at a prescribed rate through a lumen of said first device prior to said monitoring.

17. The method of claim 16 further comprising:

prescribing a slow-down force; and slowing said advancing from said prescribed rate in response to said monitoring indicating said device force as attaining a value of said slow-down force.

18. The method of claim 16 further comprising:

prescribing a stop force; and stopping said advancing in response to said monitoring indicating said device force as attaining a value of said stop force.

19. The method of claim 16 further comprising:

prescribing a first stop force, said advancing to be stopped upon said monitoring indicating said device force as attaining said first stop force when a distal portion of said source implement is within a first portion of said lumen; and prescribing a second stop force, said advancing to be stopped upon said monitoring indicating said device force as attaining said second stop force when a distal portion of said source implement is within a second portion of said lumen.

20. The method of claim 16 wherein said monitoring of said device force includes taking multiple readings of said device force during said advancing, said method further comprising:

prescribing a stop force; and stopping said advancing in response to said monitoring indicating said device force as attaining a value of said stop force in successive readings of said multiple readings.

21. The method of claim 16 further comprising identifying said first device prior to said advancing.

22. The method of claim 21 further comprising prescribing a slow-down force based upon an identity obtained from said identifying, said advancing to be slowed from said prescribed rate upon said monitoring indicating said device force as attaining said slow-down force.

23. The method of claim 21 further comprising prescribing a stop force based upon an identity obtained from said identifying, said advancing to be stopped upon said monitoring indicating said device force as attaining said stop force.

* * * * *

UNITED STATES PATENT AND TRADEMARK OFFICE
CERTIFICATE OF CORRECTION

PATENT NO. : 6,585,634 B1
DATED : July 1, 2003
INVENTOR(S) : Henckel et al.

It is certified that error appears in the above-identified patent and that said Letters Patent is hereby corrected as shown below:

<u>Title page</u>,
Item [56], References Cited, U.S. PATENT DOCUMENTS, please delete "Fishell" and insert -- Fischell --.

<u>Column 9</u>,
Line 35, please delete "s aid" and insert -- said --.

Signed and Sealed this

Thirtieth Day of March, 2004

JON W. DUDAS
*Acting Director of the United States Patent and Trademark Office*